United States Patent
Wimpenny et al.

(10) Patent No.: US 12,186,537 B2
(45) Date of Patent: Jan. 7, 2025

(54) CARTRIDGE ASSEMBLY AND METHOD FOR ASSEMBLING THE SAME

(71) Applicant: Sanofi, Paris (FR)

(72) Inventors: Steven Wimpenny, Warwick (GB); David Aubrey Plumptre, Warwick (GB); Robert Frederick Veasey, Warwick (GB); Ian McFaul, Warwick (GB); Hugh Smith, Warwick (GB); Paul Griffin, Warwick (GB)

(73) Assignee: Sanofi, Paris (FR)

( * ) Notice: Subject to any disclaimer, the term of this patent is extended or adjusted under 35 U.S.C. 154(b) by 868 days.

(21) Appl. No.: 17/258,699

(22) PCT Filed: Jul. 15, 2019

(86) PCT No.: PCT/EP2019/068970
§ 371 (c)(1),
(2) Date: Jan. 7, 2021

(87) PCT Pub. No.: WO2020/016161
PCT Pub. Date: Jan. 23, 2020

(65) Prior Publication Data
US 2021/0283333 A1    Sep. 16, 2021

(30) Foreign Application Priority Data
Jul. 18, 2018 (EP) .................................... 18305976

(51) Int. Cl.
*A61M 5/24* (2006.01)

(52) U.S. Cl.
CPC ....... *A61M 5/24* (2013.01); *A61M 2005/2403* (2013.01); *A61M 2005/244* (2013.01); *A61M 2207/00* (2013.01)

(58) Field of Classification Search
CPC .... A61M 2005/244; A61M 2005/2437; A61M 2005/2403; A61M 2005/2433;
(Continued)

(56) References Cited

U.S. PATENT DOCUMENTS

2013/0204187 A1* 8/2013 Avery ................. A61M 5/24
604/111
2018/0064877 A1  3/2018 Schneider et al.

FOREIGN PATENT DOCUMENTS

CN    102917739    2/2013
CN    103140249    6/2013
(Continued)

OTHER PUBLICATIONS

PCT International Preliminary Report on Patentability in International Application No. PCT/EP2019/068970, dated Jan. 19, 2021, 9 pages.
(Continued)

*Primary Examiner* — Nathan R Price
*Assistant Examiner* — Kayla M. Turkowski
(74) *Attorney, Agent, or Firm* — Bond, Schoeneck & King, PLLC (57) ABSTRACT

A cartridge assembly for a drug delivery device is described. The cartridge assembly includes (i) a cartridge containing a drug, the cartridge including a dispensing end; (ii) a cartridge holder, the cartridge holder defining an interior cartridge holding section, in which the cartridge is arranged within the cartridge holding section; and (iii) a fixing member. The fixing member includes a fixing surface arranged to abut a cartridge surface of the cartridge, in particular a radially oriented surface. The cartridge surface is a proximal surface which faces away from the dispensing end of the cartridge, and the cartridge surface is arranged between the dispensing end of the cartridge and the end
(Continued)

opposite of the dispensing end. The fixing member includes a securing surface which is arranged to abut a holder surface of the cartridge holder. Further, a drug delivery device and a method for assembling the cartridge assembly are described.

20 Claims, 5 Drawing Sheets

(58) Field of Classification Search
CPC .... A61M 2005/2407; A61J 1/06; A61J 1/062; A61J 1/065; A61J 1/2096
See application file for complete search history.

(56) References Cited

FOREIGN PATENT DOCUMENTS

| | | | | |
|---|---|---|---|---|
| CN | 104582760 | 4/2015 | | |
| EP | 0829268 | 3/1998 | | |
| EP | 1423079 | 7/2006 | | |
| EP | 2043708 | 12/2010 | | |
| EP | 2957308 | 12/2015 | | |
| EP | 2555815 B1 * | 11/2017 | ................ | A61J 1/16 |
| JP | H10-99434 | 4/1998 | | |
| JP | 2013-523292 | 6/2013 | | |
| JP | 2013-535282 | 9/2013 | | |
| JP | 2014-502891 | 2/2014 | | |
| WO | WO 2011/032883 | 3/2011 | | |
| WO | WO 2011/124631 | 10/2011 | | |
| WO | WO 2012/017063 | 2/2012 | | |
| WO | WO-2012017063 A2 * | 2/2012 | .............. | A61M 5/24 |
| WO | WO 2012/064258 | 5/2012 | | |
| WO | WO 2012/089620 | 7/2012 | | |
| WO | WO 2012/130704 | 10/2012 | | |
| WO | WO 2013/110769 | 8/2013 | | |
| WO | WO 2013/139894 | 9/2013 | | |
| WO | WO 2016/065220 | 4/2016 | | |
| WO | WO 2016/091554 | 6/2016 | | |
| WO | WO 2016/150900 | 9/2016 | | |
| WO | WO 2017/186435 | 11/2017 | | |
| WO | WO-2019126421 A1 * | 6/2019 | .............. | A61M 5/24 |

OTHER PUBLICATIONS

PCT International Search Report and Written Opinion in International Application No. PCT/EP2019/068970, dated Aug. 13, 2019, 12 pages.

* cited by examiner

Fig. 5        Fig. 6

CARTRIDGE ASSEMBLY AND METHOD FOR ASSEMBLING THE SAME

CROSS REFERENCE TO RELATED APPLICATIONS

The present application is the national stage entry of International Patent Application No. PCT/EP2019/068970, filed on Jul. 15, 2019, and claims priority to Application No. EP 18305976.5, filed on Jul. 18, 2018, the disclosures of which are incorporated herein by reference.

TECHNICAL FIELD

The present disclosure relates to a cartridge assembly, particularly a cartridge assembly for a drug delivery device, preferably an injection device and/or a pen-type device, such as a pen-type injector. Furthermore, the present disclosure relates to a drug delivery device comprising the cartridge assembly and a method for assembling the cartridge assembly.

BACKGROUND

In regular drug delivery devices, where a single drive mechanism which may be housed in a housing of the drug delivery device is used in conjunction with several cartridges or ampules to dispense drug or medicament contained in the cartridge or ampule from the device, usually a cartridge holder of the device is releasably connected to the housing and can be removed from the housing to replace a used cartridge. For doing so, the cartridge holder is disconnected from the housing, the used cartridge is removed from the holder and replaced with a new cartridge which is inserted into the cartridge holder, where the cartridge holder is again attached to the housing and the device is ready to be used again to dispense drug or medicament from the new cartridge.

Devices of this kind, however, do have several risks. For example, a cartridge containing a drug for which the mechanism of the drug delivery device is not specifically designed, i.e. a wrong drug or medicament, can be inserted into the cartridge holder and the user does not realize that he has put the wrong drug cartridge into the cartridge holder. This mistake may be lethal for the user and is also likely to occur as cartridges with different drugs or medicaments usually look pretty much alike. Furthermore, the cartridge, if sold as a separate item, is usually easily damaged, in particular as the standard cartridges are usually glass cartridges. Still further, in a specific cartridge holder, usually only a cartridge of one specific dimension can be retained and connected to a drive mechanism. Accordingly, cartridges of various dimensions such as of different length and/or diameter can usually not be connected to the same drive mechanism easily.

SUMMARY

It is an object of the present disclosure to provide an improved cartridge assembly for a drug delivery device and/or further improvements or configurations associated with the cartridge assembly. These objects and potentially other objects are solved by the present disclosure and, particularly, by the subject-matter of the independent claims. Advantageous embodiments and refinements are subject to the dependent claims.

One aspect of the present disclosure relates to a cartridge assembly, in particular one for a drug delivery device, such as a pen-type device and/or an injection device. Another aspect relates to the drug delivery device. The drug delivery device expediently comprises the cartridge assembly as described herein above and below and a housing. The cartridge assembly may be releasably secured to the housing. Within the housing, a drive mechanism, which is preferably designed to drive a dispensing action in order to dispense drug from the cartridge, may be retained or at least one or more elements thereof, such as a piston rod. Another aspect relates to a method of assembling a cartridge assembly.

The cartridge assembly comprises a cartridge which contains a drug or medicament. The cartridge comprises a dispensing end. Through the dispensing end, drug or medicament may be dispensed from the cartridge. The dispensing end of the cartridge may be designated as the distal end.

The cartridge assembly further comprises a cartridge holder. The cartridge holder may define an interior cartridge holding section. The cartridge holding section may be delimited by the cartridge holder, in particular by one or more parts thereof, circumferentially. The cartridge is expediently arranged within the cartridge holding section. The cartridge assembly further comprises a fixing member. The fixing member has a fixing surface, in particular a radially oriented surface. The fixing surface is expediently arranged to abut or abuts a cartridge surface of the cartridge, in particular a radially oriented surface. The fixing surface may be arranged to prevent removal of the cartridge from the cartridge holder. Thus, the cartridge may be permanently secured in the cartridge holder. The fixing surface may be arranged to prevent removal of the cartridge from the cartridge holder via an opening of the cartridge holder, preferably a proximal opening. This opening may be the one via which the cartridge is inserted into the cartridge holder, for example when assembling the cartridge assembly. The cartridge surface may be a proximal surface which faces away from the dispensing end of the cartridge. The fixing surface may be a distal surface. The cartridge surface may be arranged between the dispensing end of the cartridge and the end opposite of the dispensing end. Particularly, the cartridge surface may be a surface which is different from an end surface of the cartridge, where two end surfaces, e.g. a distal end surface and a proximal end surface, delimit the cartridge in its main longitudinal direction of extent. The fixing member may be integrated into the cartridge holder. The fixing member may be a clip member, for example.

The fixing member and, in particular, the fixing surface may abut, be arranged to abut or mechanically cooperate with the cartridge, particularly the cartridge surface, to secure the cartridge in the cartridge holder. The cartridge may be a glass cartridge. The cartridge may comprise a main body portion and a head portion which are separated by and/or connected via a neck portion, which may have a reduced diameter as compared to the main body portion and/or the neck portion. The cartridge surface may be a surface which delimits the head portion proximally, i.e. in the proximal direction. The main body portion may be cylindrical. In the head portion, the dispensing end or opening of the cartridge may be arranged. The dispensing end or opening may be closed, e.g. by a pierceable septum, which can be pierced by a needle to provide fluid communication between the interior of the cartridge and the exterior. The cartridge holder may have an opening which delimits the cartridge holder in the proximal direction. In the distal direction, the cartridge holder may be delimited by a distal end wall. A distal end face of the cartridge may be arranged to abut an interior proximal face of the cartridge holder. The proximal face may be in interior surface defined by the distal end wall. In other words, in the distal direction, the cartridge may not be moved relative to the cartridge holder. The cartridge may be secured permanently in the cartridge holder by the fixing member. Preferably, without the fixing member, the cartridge could be removed from the cartridge holder, e.g. via the proximal opening.

The fixing member may comprise a securing surface. The securing surface is expediently arranged to abut a holder surface of the cartridge holder to prevent removal of the cartridge from the cartridge holder. Therefore, the cartridge may be permanently secured in the cartridge holder by the fixing member, in particular by the fixing surface which abuts the cartridge surface and thus prevents axial movement of the cartridge relative to the fixing member in the proximal direction and by the securing surface abutting the holder surface which prevents axial movement of the fixing member relative to the cartridge holder in the proximal direction. The holder surface may be an integral surface of the cartridge holder. The holder surface may be a distal surface of the cartridge holder.

Accordingly, by means of the separate fixing member which is a separate member different from the cartridge holder and from the cartridge, the cartridge can be reliably secured in the cartridge holder. As opposed to a fixing feature which is integrated into the cartridge holder, the fixing member can be more easily designed to suit the requirements. For example, it might be formed more easily as being stable under high forces, e.g. as different materials can be used for the fixing member than for the cartridge holder. The fixing member may comprise or be made of metal or plastic. The material of the fixing member may be different from the material of the cartridge holder, e.g. a plastic. For example when a body of the same size and shape is formed from the material of the fixing member this body may be less flexible or deformable under a certain force as compared to another body of the same size and shape from the material of the cartridge holder under the same force.

Axially directed forces such as forces in the proximal direction may be reacted by the securing surface of the fixing member abutting the holder surface such that the member cannot be removed via the proximal opening of the cartridge holder. The fixing surface and the securing surface may face in opposite axial directions such that they can abut the holder surface and the cartridge surface respectively which likewise may face in opposite directions. The fixing surface may face in the distal direction and consequently be a distal surface. The securing surface may face the proximal direction and, consequently may be a proximal surface. The holder surface may be a radially oriented surface. The holder surface may be formed or defined by a radial protrusion in the interior of the cartridge holder.

As the cartridge is expediently permanently secured in the cartridge holder, the cartridge assembly may form one unit or a single unit of consumable material. That is to say, the cartridge assembly in its entirety may be a disposable item, which is disposed of after the drug in the cartridge has been dispensed, and substituted by a new cartridge assembly.

If the cartridge is permanently secured in the cartridge holder by the fixing member several advantages are attained. For example, the cartridge is always protected by the cartridge holder when the user handles the cartridge assembly. The risk of a cartridge breaking is then considerably reduced as opposed to systems where the cartridge in the holder needs to be replaced by the user. Rather, in the proposed system, the entire cartridge assembly is replaced with a new one.

Moreover, as the cartridge assembly comprises not only the cartridge but also other elements like the cartridge holder and the fixing member, it is easier to dedicate or code the cartridge to a particular drive mechanism or housing for a drug delivery device, in particular without having to change the design of the cartridge. Rather the other elements might be designed to dedicate or code the cartridge assembly to a drive mechanism.

The dedication or coding can be achieved via features provided on the exterior of the cartridge holder which may cooperate with features provided in the housing to either permit that the cartridge assembly is connected to the housing, if the drive mechanism housed in the housing matches the cartridge assembly or the drug contained therein or not if the wrong cartridge assembly is used. Alternatively or additionally, on the cartridge holder, additional information about the content of the cartridge can be presented such as the name of the active pharmaceutical ingredient, the brand name etc.

As the cartridge surface is provided between the two opposite ends of the cartridge, the disclosed concept can be used for cartridges of different lengths easily. Accordingly, a set of cartridge assemblies having at least two cartridge assemblies may have two different cartridges of different lengths in the assemblies.

Further, by means of the fixing member cartridges of different diameters or lengths may be secured in a standard cartridge holder, where the respective fixing member might be used to take account for the different dimensions. Cartridges of different lengths or diameter may have different volumes. Accordingly, the disclosed concepts are suitable to secure cartridges of different volumes in the cartridge holder.

In an embodiment, the fixing member has a main body. The main body may have a ring-like shape. An axial opening may extend axially through the main body. The opening may extend through the entire main body, e.g. from the distal end to the proximal end. The axial opening may be a central opening. The main body may be circumferentially or angularly closed or be interrupted by an opening, e.g. a radial opening. A section of the cartridge, for example the neck portion may be arranged within the axial opening. The radial width or diameter of the head portion of the cartridge is expediently greater than the radial width or diameter of the axial opening. Specifically, the outer diameter of the head portion may be greater than the minimum diameter of the axial opening. In the region of the minimum diameter, the fixing surface of the fixing member may be provided. The fixing surface may be one continuous surface of the fixing member or the main body. Alternatively, sections of the fixing surface may be formed by one or more fixing features. The fixing features may extend axially in the distal direction from the main body. The fixing features may be flexible and/or elastic. The fixing features may be radially deflectable, preferably resiliently, in order to increase the diameter of the opening defined between them. This allows the head portion of the cartridge to pass through the opening from the proximal direction, where, after the head portion has passed through the opening, the fixing features move radially inwardly again and are arranged to abut the proximal surface of the head portion, which may be the cartridge surface.

In an embodiment, the main body has or defines a radial opening. The radial opening may extend in the radial direction. The radial opening may extend radially away from the axial opening. The radial opening may be connected to the axial opening. Particularly, the main body may be interrupted by the radial opening. That is to say, the radial opening may extend through the entire sidewall of the main body in the radial direction. The radial opening may be delimited in the angular or azimuthal direction by angular surfaces of the main body. The radial opening facilitates the mounting of the fixing member to the cartridge utilizing a radial or lateral relative movement between cartridge and fixing member towards one another.

In an embodiment, the width of the radial opening in the cartridge assembly is less than the width of the head portion and/or the neck portion. Accordingly, it can be assured that the neck portion cannot travel through the radial opening easily from a region inside the axial opening to the outside and/or disassembling the fixing member from the cartridge is made more difficult.

In an embodiment, the fixing member is flexible and/or deformable such as elastically deformable. The fixing member may be flexible and/or deformable in the radial direction. The main body and/or the fixing features may be flexible and/or deformable. In particular, the width of the radial opening in the main body which extends in the radial direction may be varied by means of deforming or flexing the fixing member such as its main body. In this way, assembling the fixing member to the cartridge may be facilitated. However, once the cartridge assembly has been assembled, the width of the radial opening, which may be defined by the distance between the angular faces delimiting the opening, is expediently less than the width or diameter of the neck portion. The radial opening facilitates a radial mounting of the fixing member to the cartridge, preferably before the cartridge with the pre-mounted fixing member is inserted into the cartridge holder to assemble the cartridge assembly.

In an embodiment, the fixing member is axially rigid. The fixing member or a section thereof may be radially deformable. However, if exposed to axially directed forces, such as forces in the proximal direction, the fixing member is preferably rigid, e.g. it does not decrease in length. This facilitates retention of the cartridge within the cartridge holder without a possibility to remove the cartridge from the cartridge holder via the proximal opening.

In an embodiment, the holder surface protrudes in the inward direction, particular the radial inward direction, from an inner wall of the cartridge holder.

In an embodiment, the holder surface extends uniformly in the circumferential direction. The holder surface may be a continuous surface such as a, preferably closed, ring surface. That is to say, the holder surface may be a surface without interruptions. This configuration provides a uniform bearing surface for the fixing member.

If, alternatively, the holder surface is distributed over a variety of sections or interrupted, the sections of the holder surface are expediently uniformly distributed in the angular or circumferential direction such that the distances between two arbitrary adjacent sections are equal. The distances between two arbitrary adjacent sections of the holder surface are or the distance between two adjacent ends of the continuous holder surface is expediently less than the smallest angular extension of a, preferably of any, continuous section of the securing surface of the fixing member. Thus, if the securing surface is distributed over a variety of sections or interrupted in the circumferential direction, it can be assured that the section(s) of the securing surface always abuts or is arranged to abut a section of the holder surface without any possibility of the fixing member being displaced in the proximal direction relative to the holder surface, regardless of the relative angular orientation of fixing member and holder surface.

In an embodiment, the securing surface is a continuous surface and/or distributed over a plurality of sections. The sections of the securing surfaces are expediently axially aligned. That is to say, they are arranged at the same axial position. The sections may be angularly offset.

In an embodiment, as seen in the axial direction, the fixing member extends between the cartridge surface and the holder surface and/or is restricted to the region defined between the holder surface and the cartridge surface.

In an embodiment, the cartridge holder has at least two interior regions of different inner diameters or clear spans, a first region and a second region. In the first region, the head portion of the cartridge may be arranged. The second region may be axially offset from the first region in the proximal direction or towards the proximal opening of the cartridge holder. The first region may have a smaller inner diameter or clear span than the second region. The fixing surface of the fixing member may be arranged in the first region. In the second region, the main body portion of the cartridge may be arranged. The holder surface of the cartridge holder is expediently arranged in that interior region where the securing surface is arranged. The first region may be delimited by the holder surface in the proximal direction. The respective interior region may have a constant diameter.

In an embodiment, the securing surface of the fixing member is arranged in the second region. Accordingly, the fixing member may extend from the first to the second region.

If the securing surface is arranged in the region with greater diameter, axial forces which may be exerted on the cartridge when attempting to remove the cartridge from the holder in the proximal direction may be distributed over a greater area, as the holder surface may be formed more easily with a greater angular and/or radial extension in the second interior region than in the first interior region.

In an embodiment, the securing surface of the fixing member is arranged in the first region. The holder surface may delimit the first region proximally and/or provide a transition region between the first region and the second region. The inner diameter or clear span of the transition region may be less than the one in the first region and in the second region. If the securing surface is arranged in the first region, the securing surface may be arranged further away from the proximal end of the cartridge holder, which makes the fixing member less prone to manipulations from the proximal end.

In an embodiment, the axial extension of the fixing member is smaller than the distance between the head portion and the main body portion of the cartridge and/or smaller than the axial extension of the neck portion. Thus, the entire fixing member may be restricted to the neck portion axially.

In an embodiment, the fixing member comprises one or a plurality of securing features. The securing features may be circumferentially or angularly disposed, for example along the main body of the fixing member. The securing features may be uniformly disposed such that the distances between two adjacent securing features on the main body may be equal. Further, the angular extension of the securing features may be equal. Each securing feature may define one section of the securing surface. The respective securing feature may be oriented in the radial direction and/or the axial direction. The securing features may extend radially outwardly with respect to the main body and/or axially in the proximal direction. Consequently, the securing features may extend axially and radially away from the main body of the fixing member. In other words, the respective securing feature may be oriented obliquely with respect to the axial direction and the radial direction. The respective section of the securing surface may be formed by a proximal surface of the securing feature. If the securing features extend radially outwardly and proximally, the securing features tend to move radially outwardly if the securing features abut the holder surface, and the axial force is increased in the proximal direction, thus tending to increase the diameter of the fixing member in the region with the securing features. As this is expediently prevented by a lateral sidewall of the cartridge holder, the force which would be required to remove the cartridge from the cartridge holder may be increased considerably.

In an embodiment, the securing features are flexible, for example in the radial direction. They may be rigid axially, i.e. not deformable when exposed to forces in the axial direction. The securing features may be resiliently deflectable, particularly in the radial direction.

In an embodiment, the fixing member comprises an axially extending bearing surface. The bearing surface may be arranged to bear and/or bear against the neck portion of the cartridge. The bearing surface may face towards the cartridge. The bearing surface may have an axial extension which is less than or equal to the axial extension of the neck portion. The axial extension of the neck portion may be defined by the distance between the proximal end of the head portion and the distal end of the main body portion. The bearing surface may be a continuous surface as seen in the angular or circumferential direction. The bearing surface may be arranged radially between an outer surface of the cartridge and the securing features. The bearing surface may extend in the angular direction along a plurality of securing features, preferably along all securing features. In the region of a securing feature, the fixing member may have a V-like cross section where the section is taken along the axis, e.g. the axis of the cartridge. By the bearing surface, the relative position between the fixing member and the cartridge may be stabilized, particularly if the fixing member is subjected to a proximally directed force, e.g. when attempting to withdraw the cartridge from the cartridge holder.

In an embodiment, a slit is formed between two adjacent securing features. The slit may provide radial flexibility to the securing features, such that the respective securing feature may be radially deflected, e.g. radially inwardly and/or outwardly deflected, for example relative to the main body. When introducing a sub-assembly comprising the fixing member and the cartridge where the fixing member is assembled to the cartridge already, into the cartridge holder, the securing features may be deflected in the radial inward direction and, once the holder surface has been passed by the securing surface, deflect radially outwardly in order to be arranged to abut the holder surface. Thus, the assembling of the cartridge assembly is facilitated by means of the slit.

In an embodiment, the fixing surface is a continuous surface. The fixing surface may be a single continuous surface. The fixing surface may have an annular configuration, which may be interrupted, for example on account of the radial opening.

In an embodiment, the fixing surface is distributed over a plurality of sections. The sections may be circumferentially disposed and preferably uniformly distributed in the angular or circumferential direction. The respective section may be formed by a distal surface of a fixing feature. The respective fixing feature may be flexible in the radial direction and/or resiliently deflectable.

In an embodiment, the holder surface delimits an opening in a sidewall of the cartridge holder, preferably in the proximal direction. The sidewall may connect the distal end of the cartridge holder with the proximal end, where the proximal opening may be disposed. The opening in the sidewall may extend through the entire sidewall in the radial direction. Thus, the opening may provide communication between the exterior of the cartridge holder and the interior. The opening may be oriented in the angular direction. That is to say, its angular extension may be greater than its axial extension, for example. The holder surface may delimit the opening in the sidewall of the cartridge holder in the proximal direction. Accordingly, the fixing surface may interact with the holder surface within the region of the opening.

In an embodiment, the opening in the sidewall is designed to receive the fixing member. Thus, the dimension of the opening, in particular its angular dimension, may be adjusted to the dimension of the fixing member. The opening may be designed to receive the fixing member such that at least a section of the fixing member can be guided through the opening from outside of the cartridge holder to within the cartridge holder. That section may define or may comprise the section of the fixing surface which is arranged to abut the cartridge surface. Thus, the fixing surface may be formed by a section of the fixing member outside of the opening but within the cartridge holder. The securing surface may be formed by a section of the fixing member within the opening and/or arranged to abut a surface continuing in a plane fashion from the opening in the radial inward direction into the interior of the cartridge holder.

In an embodiment, the fixing member has a U-like shape. The fixing member may, for example be formed by a bent wire.

In an embodiment, the fixing member and/or its main body may have two angular free ends which face one another.

In an embodiment, in the region of free angular ends of the main body of the fixing member, protrusions may be formed, e.g. radial protrusions, which may stabilize the connection between fixing member and cartridge. For example, the protrusions may provide bearing surfaces or interaction surfaces which, when they abut a surface of the cartridge and radial movement is continued, are deflected outwardly and after having passed the neck portion are deflected again inwardly.

In the method for assembling the cartridge assembly for a drug delivery device, the cartridge is provided as are the fixing member and the cartridge holder. Thereafter, the cartridge is secured within the cartridge holder by means of the fixing member.

In an embodiment, the fixing member is assembled to the cartridge to form a sub-assembly and, thereafter, the sub-assembly is inserted into the cartridge holder. The fixing member may be, preferably radially, resiliently biased and/or, preferably radially, deformed by mechanical cooperation with the cartridge holder before the sub-assembly reaches an end position in the cartridge holder. The bias may be reduced again, for example by an elastic restoring force, which may tend to re-establish the non-deformed or non-deflected shape of the fixing member, after the deformation has taken place and before or when the sub-assembly reaches the end position within the cartridge holder.

In an embodiment, the cartridge is inserted into the cartridge holder and, thereafter, the fixing member is guided through an opening in the sidewall of the cartridge holder.

Thus, the fixing member may be connected by a radial movement to the cartridge, which is already arranged within the holder.

In an embodiment, the cartridge surface is arranged closer to the dispensing end than to an end opposite of the dispensing end, i.e. the proximal end. This facilitates securing cartridges of different lengths in the cartridge holder and/or provides the fixing member or fixing surface in a region which is not easily accessible from the outside, i.e. a region which is further away from the proximal opening or end of the cartridge holder than from the distal end of the cartridge holder. The cartridge surface may be arranged further away from the proximal end than ⅔*L, ¾*L, ⅘*L, where L is the total length of the cartridge. The length of the cartridge may be defined or determined by the distance between the proximal end of the cartridge and the distal end or dispensing end.

In an embodiment, the cartridge surface is a surface which delimits the head portion axially, in particular in the proximal direction. The cartridge surface may extend circumferentially, e.g. flange-like.

In an embodiment, the end of the cartridge opposite of the dispensing end is closed via a movable bung or stopper. If the bung or stopper is displaced within the cartridge towards the dispensing end, drug may be dispensed from the cartridge, provided fluid communication is established between the interior of the cartridge and the outside, e.g. by a needle piercing through the septum. The bung or stopper may be retained within the main body portion of the cartridge. Accordingly, as the cartridge surface with which the fixing surface or fixing member should interact may be located at the head portion, the main body portion of the cartridge can be freely designed, such as with respect to length and/or diameter. This facilitates fixing or securing cartridges of different volumes in the cartridge holder. The bung or stopper expediently sealingly closes the cartridge proximally. The bung may be restricted to travel within the main body portion. That is to say, it may not enter the neck portion and/or the head portion.

In an embodiment, the cartridge assembly comprises at least one connection feature, which is configured to be connected to a housing which may retain a drive mechanism, e.g. a feature for a threaded connection or a bayonet connection.

In an embodiment, the cartridge assembly comprises at least one interface or coding feature which is configured to cooperate with a corresponding interface or coding feature on the housing. The connection feature and the interface or coding feature may be formed by the same feature or by different features. By means of the interface or coding features, a coding can be achieved such that the cartridge assembly can only be assembled to a housing with a matching coding feature. This increases the safety for the user and it ensures that the drive mechanism which is designed to dispense a specific drug or specific amounts of drug and the content of the cartridge in the cartridge assembly match. If the cartridge assembly and the drive mechanism do not match the interface or coding features on the housing and the cartridge assembly are incompatible and the cartridge assembly cannot be connected to the housing to form a drug delivery device.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge assembly or the drug delivery device. "Proximal" may refer to a direction away from the dispensing end or an end which is or is to be arranged further away from the dispensing end of the cartridge, the cartridge assembly or the drug delivery device.

The terms "axial", "radial", "angular", or "azimuthal" as used herein may be used with respect to a main longitudinal axis of the device, cartridge, or cartridge assembly, e.g. the axis which extends through the proximal and distal ends of the cartridge assembly, the cartridge or the drug delivery device.

Features disclosed above in conjunction with the cartridge assembly, the drug delivery device, or the method should not be regarded as referring to only the recited aspect or embodiment. Rather, the features also apply for other embodiments or aspects. Features disclosed in conjunction with the assembly do also apply for the method and for the device and vice versa, for example. Of course, features disclosed in specific embodiments, be it above or further below, can also be applied in combination with one another and/or with other features of other embodiments.

Further features, advantages and expediencies of the present disclosure become apparent from the following description of the exemplary embodiments in conjunction with the drawings.

BRIEF DESCRIPTION OF THE FIGURES

FIGS. 1A through 1C illustrate an embodiment of a cartridge assembly, where

FIGS. 2A and 2B illustrate another embodiment of a cartridge assembly, where

FIGS. 3A and 3B illustrate another embodiment of a cartridge assembly, where

FIGS. 4A through 4C illustrate yet another embodiment of a cartridge assembly, where

DETAILED DESCRIPTION

Identical elements, elements of the same kind and identically acting elements may be provided with the same reference numerals throughout the figures.

In the following, in conjunction with the drawings, several embodiments of cartridge assemblies with fixing member, which secure the cartridge in the cartridge holder of the assembly are disclosed. Before the specifics of the respective embodiments are disclosed, features which apply to all embodiments are discussed. FIGS. 1A through 1C, 2A and 2B, 3A and 3B, as well as 4A through 4C each illustrate one embodiment of a cartridge assembly 300.

The cartridge assembly 300 comprises a cartridge 301 and a cartridge holder 302. The cartridge 301 is arranged within a cartridge holding or retaining section 303 of the cartridge holder. The cartridge retaining section is expediently delimited by an inner wall 304 of the cartridge holder 302, preferably circumferentially. The cartridge holder 302 has an opening 305 (see FIG. 3A or 4A). The opening 305 is expediently a proximal opening. The proximal opening may provide access to the interior of the cartridge holder from the proximal end of the holder. Via the opening 305, the cartridge 301 can be inserted into the cartridge holder 302. A dispensing end 306 of the cartridge may be inserted or introduced into the cartridge through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305. The axial extension of the cartridge holder is expediently chosen so as to cover at least 50%, preferably more than 60% or more than 70% such as more than 80% or more than 90% of the total length of the cartridge. The entire cartridge may be covered by the cartridge holder 302.

The end of the cartridge opposite to the dispensing end 306, i.e. the proximal end, is not illustrated explicitly in the figures. This end may be closed by a movable bung or stopper, which is likewise not explicitly illustrated. The bung or stopper may sealingly close a proximal opening of the cartridge. A drug 307 or medicament is contained in that region of the cartridge which is arranged between the dispensing end and the bung. Drug may be dispensed through the dispensing end 306 from the cartridge, if fluid communication between the interior of the cartridge and the exterior is provided and the bung is moved towards the dispensing end. The amount of drug 307 in the cartridge is preferably sufficient for a plurality of doses, where the size of the dose may be set by the user or may be fixed, e.g. by the design of the drive mechanism used to deliver the drug or medicament from the drug delivery device which comprises the cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

On the side of the dispensing end 306, the interior of the cartridge which holds the drug or medicament 307 is sealingly closed by a septum 308. The septum 308 may be retained at or fixed relative to a cartridge body 340 of the cartridge by means of a septum retainer 309. The septum 308 is expediently pierceable, e.g. via a needle, which may provide fluid communication between the interior of the cartridge and the exterior. The septum retainer 309 may be formed by a cap, e.g. a metal cap, such as an aluminum cap. The metal cap may be connected via clamping or crimping to the cartridge body 340. The body of the cartridge may be formed of glass. The body may define the outer contour of the cartridge. In the region of the dispensing end 306, where the needle should penetrate the septum, an opening is provided in the septum retainer 308 to allow the needle to pass through the region of the septum retainer. The cartridge 301 comprises a head portion 310 and a main body portion 311. The head portion 310 is arranged on the side of the dispensing end 306. The main body portion 311 may be arranged closer to the proximal end of the cartridge than the head portion 310. Between the head portion 310 and the main body portion 311 a neck portion 312 may be arranged. The main body portion 311 may be that region, where the bung or stopper may travel. The main body portion has a tubular configuration. The neck portion 312 may have a reduced diameter, outer and/or inner diameter, as compared to the main body portion 311. The head portion 310 has a reduced diameter, outer and/or inner diameter, as compared to the main body portion 311. The neck portion 312 has a reduced diameter as compared to the main body portion and also with respect to the head portion 310. The diameter may be the extension of the cartridge in a direction perpendicular to the main longitudinal axis of the cartridge or the cartridge assembly which extends between the proximal end and the distal end. The neck portion may extend circumferentially. The entire cartridge may be rotationally symmetric relative to the main longitudinal axis. The transition between the head portion 310 and the neck portion 312 may be formed via a comparatively steep surface, which is preferably less inclined relative to the radial direction than the surface which is provided between the neck portion 312 and the main body portion 311. Accordingly, the transition between the neck portion 312 and the main body portion 311 may be less steep than the one between the head portion 310 and the neck portion 312. Specifically, a cartridge surface 313, which may delimit the head portion 310 proximally, may have an inclination relative to the radial direction which is less than the inclination of a shoulder surface 314 which delimits the main body portion distally. The cartridge surface may be formed by the septum retainer 309 or, alternatively by the cartridge body. The septum retainer 309 may clamp the septum to the cartridge body. Thus, the septum retainer may extend from the distal end along the cartridge to a surface of the neck portion of the cartridge body facing away from the distal end of the cartridge and extending in the radial direction to clamp the septum 308 to the cartridge body. The cartridge may comprise or consist of the cartridge body 340, the septum 308, the septum retainer 309, the drug 307, and/or the bung (not explicitly illustrated).

The cartridge holder 302 comprises on that end opposite of the opening 305 and/or closest to the dispensing end 306 of the cartridge, i.e. its distal end, a distal end wall 315. The distal end wall may extend circumferentially in a ring-like fashion. A proximal surface of the distal end wall 315 is arranged to abut the distal end face of the cartridge 301. In this way, the cartridge 301 can be retained in the cartridge holder without moving distally relative to the cartridge holder 302. The distal end wall 315 may define an opening 316 in the cartridge holder. The end wall may extend around the opening such that the opening is a central opening in the end wall. The opening may extend axially through the end wall 315. The opening 316 may be provided such that a needle can be guided through the opening towards the cartridge, in particular towards the septum 308.

The cartridge holder 302 may comprise a distal region 317 and a main body region 318. The distal region 317 is arranged closest to the dispensing end of the cartridge and/or to the distal end wall 315 of the cartridge holder. The main body region 318 is arranged further away from the distal end or the distal end wall 315 and/or closer to the opening 305 than the distal region. As compared to the main body region the distal region may have a reduced outer diameter. The reduction may be determined by the reduced diameter of the head portion as compared to the diameter of the main body portion of the cartridge. The main body region 318 and the distal region 317 may be connected by an inwardly directed shoulder region 331. In the distal region a needle connector 319, for example a thread may be arranged. Via the needle connector, a needle unit, for example a hub of a needle unit may be secured to the cartridge holder 302. A needle retained in the needle hub may be guided through the opening 316, pierce the septum 308 and provide fluid communication to the interior of the cartridge to dispense drug 307 from the cartridge 301. The distal region 317 may be designed to receive the head portion 310 of the cartridge 301 in its interior. The main body region 318 may be designed to receive the main body portion 311 of the cartridge. On the side of the proximal end the cartridge holder may have a connection or interface region 320. In that region, connection or interface features may be provided, which are configured to cooperate with corresponding features on a housing 10 to connect the cartridge assembly 300 to the housing to form a drug delivery device 1 (see FIGS. 5 and 6). The connection features may be designed for a threaded or bayonet connection between cartridge holder and housing. Preferably, the connection or interface features are coded to a housing which houses a drive mechanism designed for the drug contained in the cartridge of the cartridge assembly. The coding ensures that only a correct cartridge assembly can be assembled to the housing to form a drug delivery device. In this way, it can be guaranteed that the drug in the cartridge assembly is dispensed using a drive mechanism which is specifically designed to dispense the content of the cartridge. The drive mechanism may comprise a piston rod, which is arranged to drive the bung or stopper distally relative to the cartridge, if drug should be dispensed from the cartridge.

Between the proximal end and the distal end of the cartridge holder 302, preferably closer to the proximal end than to the distal end, a radially outwardly protruding step 321 or flange, may be provided. The step or flange 321 may extend over the entire circumference of the cartridge holder 302. A proximal surface of the step 321 may be arranged to contact a distal surface of the housing when the cartridge assembly is connected to the housing. The connection region 320 may be covered by the housing, when the assembly has been connected to the housing. The main body region 318 and the distal region 317 may, however, protrude from the housing. Moreover, the cartridge assembly 300 comprises a fixing member 322. The fixing member 322 is expediently permanently retained within the cartridge assembly or the cartridge holder and, particularly preferably, not accessible from the outside. The fixing member 322 may be retained in the cartridge assembly at a position which is remote from the proximal opening 305 of the cartridge holder 302. The fixing member 322 may be a plastic component or a metal component. The cartridge holder 302 in the embodiments may be a unitary part. The cartridge holder 302 may be an injection molded part.

The fixing member 322 comprises a fixing surface 323. The fixing surface 323 is oriented in the distal direction, i.e. a distal surface, and, particularly faces the cartridge surface 313, which may be formed by the septum retainer 309 or the neck portion of the cartridge body, respectively. The fixing surface 323 may be arranged to abut or already abut the cartridge surface. If it is attempted to move the cartridge proximally relative to the cartridge holder 302, an abutment between the cartridge surface 313 and the fixing surface 323 is expediently established. The fixing member 322 furthermore comprises a securing surface 324. The securing surface 324 may be a surface which faces away from the dispensing end 306 of the cartridge. The securing surface 324 is preferably a proximal surface. The securing surface 324 is arranged to abut a holder surface 325 of the cartridge holder 302. The holder surface 325 is a distal surface. Accordingly, if the fixing member abuts the holder surface and the cartridge surface by means of the fixing surface and the securing surface, it can be ensured that the cartridge 301 cannot be removed in the proximal direction via the opening 305 from the cartridge holder 302. Thus, the force exerted on the cartridge is transferred to the fixing member via the cartridge surface abutting the fixing surface and reacted by the cartridge holder via the abutment of the securing surface and the holder surface. The fixing member 322 is formed as a separate component, which is provided in addition to the cartridge and the cartridge holder. By means of a fixing member, differences between different cartridges can be accounted for where these cartridges can nevertheless be secured within the cartridge holder by the same fixing member. The fixing member 322 is expediently axially rigid. That is to say, it cannot easily or not at all be axially deformed. The axial extension of the fixing member may be constant. Thus, the fixing member 322 is able to withstand axial forces exerted on the fixing member, for example if the cartridge is attempted to be removed from the cartridge holder of the cartridge assembly. The fixing member may be radially flexible and/or deformable, preferably elastically.

Figure 1A:
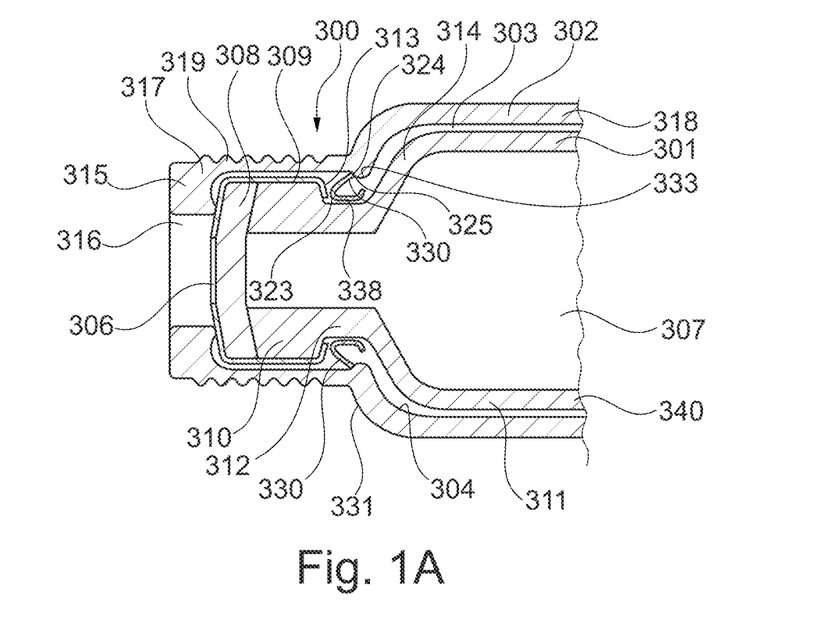
FIG. 1A shows a sectional view of a distal portion of the cartridge assembly.
Figure 1B:
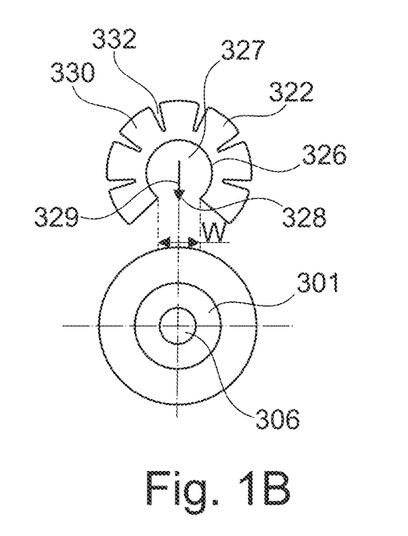
FIG. 1B illustrates the mounting process of the fixing member to the cartridge in a top view.
Figure 1C:
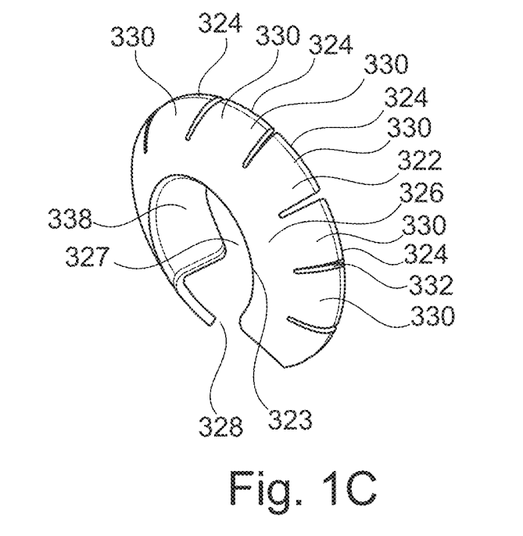
FIG. 1C illustrates the fixing member in a perspective view.

In the embodiment illustrated in conjunction with FIGS. 1A through 1C, the fixing member has a main body 326. The main body 326 has a generally ring-like configuration in particular as seen in top view. This is for example apparent from the top view shown in FIG. 1B, which illustrates the assembling process of how the fixing member 322 is assembled to the cartridge 301. An axial opening 327 extends through the entire main body or the entire fixing member from the proximal end to the distal end of the fixing member. The generally ring-like main body 326 is interrupted by a radial opening 328. The radial opening extends in the radial direction through the main body and may be delimited in the angular direction by angular side faces formed by means of the main body. The axial opening 327 is expediently designed to receive the neck portion 312 of the cartridge 301 when the fixing member 322 has been assembled to the cartridge. As depicted in FIG. 1B, the fixing member can be assembled to the cartridge by a lateral or radial movement. For doing so, the fixing member is guided towards neck portion of the cartridge, which may pass through the radial opening. The radial direction is indicated by arrow 329. Thereby, the fixing member may be radially deformed, when contacting the outer perimeter of the neck portion in order to increase the width of the radial opening 328. In the non-deformed state, the radial opening preferably has a width which is less than the one of the neck portion. When the neck portion has passed through the radial opening, the neck portion may be received in the axial opening. During the transition of the neck portion 312 from the region of the radial opening 328 into the axial opening 327, the fixing member may relax and resume its original shape, e.g. due to an elastic restoring force causing movement of the fixing member which reduces the width of the radial opening again. In FIG. 1B, the width of the radial opening is designated with "W".

The fixing member 322 further comprises a plurality of securing features 330. The securing features are disposed circumferentially along the main body 326. The securing features may be formed finger-like or tab-like. More than four securing features 330 may be provided. The securing features may be oriented obliquely relative to the axial and the radial direction. As depicted in FIG. 1A, the securing features 330 may be oriented at about an angle of greater than 30 degrees relative to the axial direction and/or the radial direction. The inclination angle relative to the radial and the axial direction may be 45°, for example. Adjacent securing features may be separated by a slit 332, which extends between two securing features and is oriented towards the main body. The angular extension of the slit may be less than the angular extension of the securing features. Each of the securing features comprises a section of the securing surface. The securing features have free ends. The section of the securing surface may be defined at the free end of the securing features. The securing features may be resiliently deformable in the radial direction. Accordingly, once having been deflected inwardly, they may tend to be moved outwardly on account of their resiliency. After the fixing member 322 has been assembled to the cartridge, for example by a radial movement as depicted in FIG. 1B, the sub-assembly comprising the cartridge and the fixing member may be inserted into the cartridge holder 302 via the proximal opening 305.

The holder surface 325 may be a distal surface. The holder surface may originate from an inner wall of the cartridge holder and extend radially away from that wall. The holder surface 325 may be defined by a protrusion 333 which protrudes radially inwardly from the inner wall 304 of the cartridge holder. The holder surface 325 and/or the associated protrusion may extend circumferentially along the entire circumference of the interior of the cartridge holder 302. The holder surface may form a full ring. The diameter of the opening defined in the region of the protrusion may be greater than the outer diameter of the neck portion and less than the maximum outer diameter of the fixing member and/or less than the outer diameter of the fixing member in the region with the securing features 303. Accordingly, when the securing features contact the protrusion 333 from the proximal side, they are radially deflected inwardly until the securing surface 304 has passed the protrusion. Then the securing features deflect again radially outwardly as it relaxes again. Once having been deflected outwardly, the cartridge may have reached its final position within the cartridge holder. Then, the securing surface prevents removal of the cartridge from the cartridge holder. Alternatively or additionally, the radial opening may reduce its width while the fixing member travels along the protrusion 333. In the final position, the radial opening may resume its original width.

In the region adjacent to the neck portion 312, the fixing member may comprise an axially extending bearing surface which bears against the neck portion 312. The bearing surface is designated with reference numeral 338 in FIGS. 1A and 1C, for example. The bearing surface may extend circumferentially and may in the angular direction cover more than one securing feature preferably all securing features. The bearing surface 338 may be arranged radially between an outer surface of the cartridge 301 and the securing features 324.

The fixing member 322 is a clip component with an approximately U-like shape, as seen in top or plan view. The securing features may extend from a distal surface of the fixing member 322, e.g. the fixing surface, in the proximal direction. The fixing member 322 can be formed by means of a metal pressing. The fixing member 322 can be attached to the cartridge 301 from the radial direction with a relative low assembly force. This is unlikely to damage the cartridge body, e.g. of glass, the septum or the septum retainer. Once in the final position, the cartridge is very stably retained against axial removal of the cartridge from the cartridge holder.

In this embodiment, the holder surface 325 and/or the associated protrusion 333 are located between an interior region of the cartridge holder which is intended to receive the head portion 310 and an interior region which is intended to receive the main body portion 311. Particularly, a region of the interior the inner diameter of which is adjusted to the outer diameter of the head portion may be delimited by means of the holder surface 325 in the proximal direction.

The holder surface 325 may be formed by "bumping" the cartridge holder off a core pin in the molding process, where the core pin defines an interior of the cartridge holder. This may be done during the molding process using a suitable ejection feature in the molding tool.

Figure 2A:
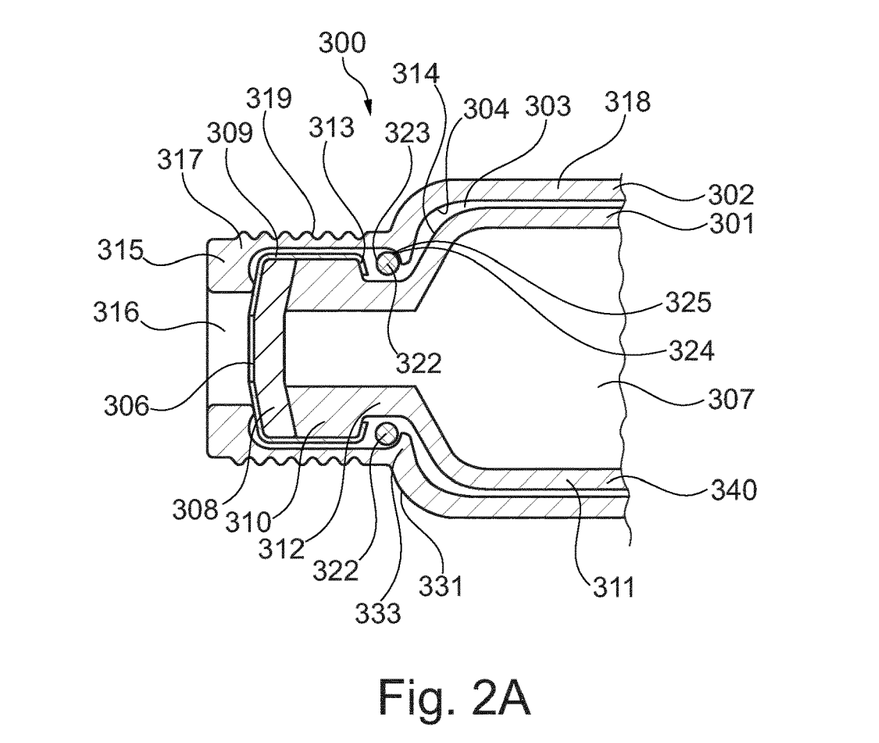
FIG. 2A shows a sectional view of a distal portion of the cartridge assembly.
Figure 2B:
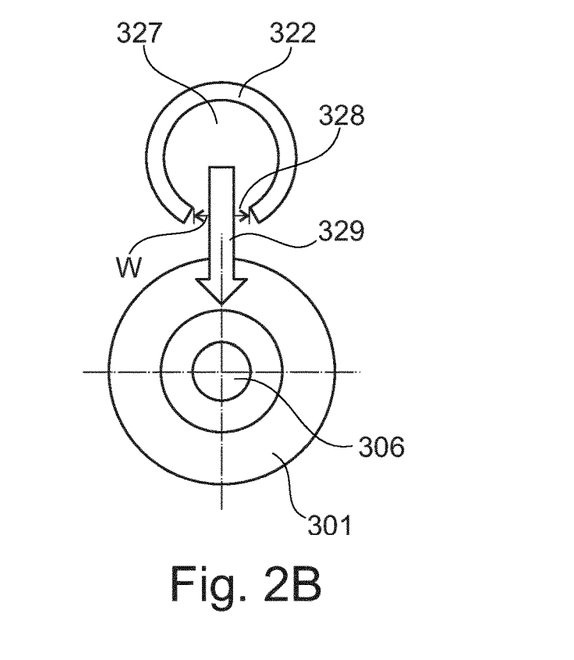
FIG. 2B illustrates the mounting process of the fixing member to the cartridge in a top view.

The embodiment depicted in FIGS. 2A and 2B is similar to the one discussed above in connection with FIGS. 1A through 1C. Thus, the description is not repeated in its entirety but it is focused on the differences. As opposed to the previous embodiment, the fixing member 322 does not comprise the securing fingers or features 330. Rather, the fixing member 322 is formed ring-like with a radial opening 328 and an axial opening 327. The fixing member may have a U-like shape. The fixing member 322 may be formed by means of a bent wire. Aside from that, the fixing member 322 functions as described previously. Thus, the fixing member 322 can be formed by a simple wire forming process.

When the sub-assembly with the cartridge and the fixing member is axially guided into the cartridge holder via the proximal opening, the fixing member abuts the proximal surface of the protrusion, is radially deformed such that the width of the radial opening is reduced. Once the securing surface has passed the holder surface, the fixing member 322 resumes its original, e.g. U-like, shape and the securing surface 324 is arranged to abut the holder surface 325 as depicted in FIG. 2A.

As in FIGS. 1A through 1C, the axial extension of the fixing member 322 is defined by, equal to or even less than the axial extension of the neck portion.

Figure 3A:
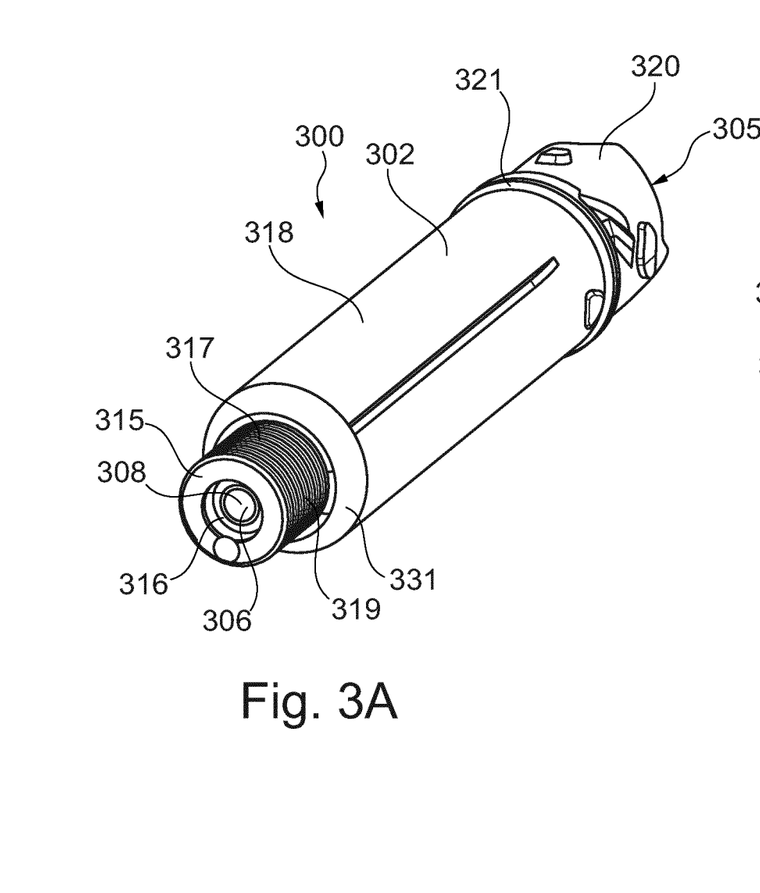
FIG. 3A shows a perspective view of the cartridge assembly.
Figure 3B:
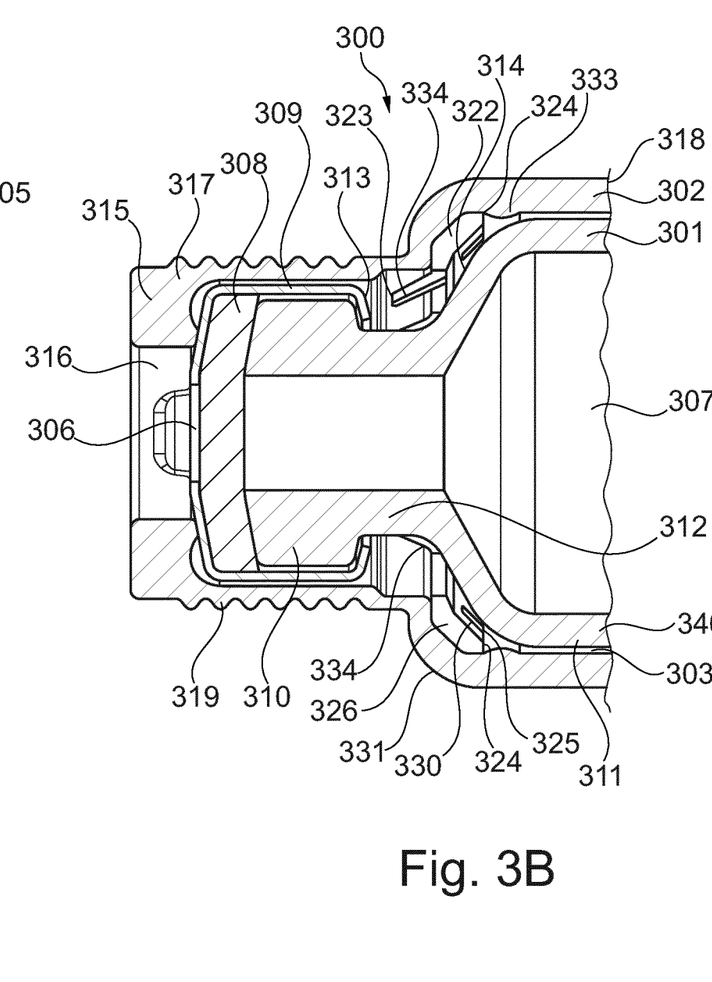
FIG. 3B shows a sectional view of a distal portion of the cartridge assembly.

The embodiment depicted in FIGS. 3A and 3B also largely correspond to the ones discussed previously in conjunction with FIGS. 1A through 2B. Thus, the description is not repeated in its entirety but it is focused on the differences. The fixing member 322 comprises a plurality of securing features 330 which are oriented obliquely relative to the main body and extend in the proximal direction. One section of the securing surface 324 is associated with or formed by each securing feature or finger. This corresponds to the embodiment in FIG. 1. However, the protrusion 333 and/or the holder surface 32 is defined in the interior of the main body region 318 of the cartridge holder 302 and not in the interior of the distal region 317 as in FIG. 1. Still further, the main body 326 may form a full ring, i.e. it is closed in the radial direction over its entire circumference.

Accordingly, for assembling the fixing member 322 to the cartridge, a relative axial movement may need to be performed for securing the fixing member to the cartridge as no radial opening is present. For securing the cartridge and the fixing member stably to one another, the fixing member comprises one or more fixing features 339. The fixing features 339 may be formed as fingers and extend radially, preferably inwardly and/or distally, from the main body 326. The fixing features 339 may be elastically deflectable. An opening defined by the fixing features may have a diameter which is less than the one of the head portion 310 of the cartridge 301. Accordingly, when the cartridge is introduced into this opening, the head portion interacts with the fixing features 339 and the features 339 are deflected radially outwardly. Then, after the head portion has passed the fixing features, on account of their resiliency, the fixing features 339 deflect again inwardly and are arranged to abut the cartridge surface 313. The plurality of fixing features 339 may be uniformly distributed in the rotational or angular direction.

The holder surface 325 may, again, be defined by the distal surface of the circumferential protrusion 333 which is formed in the cartridge holder during the molding process, e.g. by bumping off a core pin as previously disclosed. Insertion of the sub-assembly comprising the fixing member and the cartridge into the cartridge holder may take place as described previously. The fixing member 322 may be a plastic molding or a metal pressing. The fixing member 322 is relatively flexible in the unassembled condition which allows it to be assembled to the cartridge with a very low force which is unlikely to damage the septum retainer or the (glass) cartridge body. Once the sub-assembly with the cartridge and the fixing member has been introduced into the cartridge holder, the securing features engage the holder surface 325.

The geometry of the securing features 330 is chosen such that if the cartridge 301 is attempted to be removed from the cartridge holder 302, the force applied to the fixing member causes or tends to cause the securing features to deflect radially outwardly, e.g. until they hit or abut the holder surface 325 and the inner wall of the cartridge holder. Thereby, the positive engagement with the holder surface may be even strengthened. Accordingly, although the fixing member may be a relatively thin and flexible component, it nevertheless provides a high retention force.

Figure 4A:
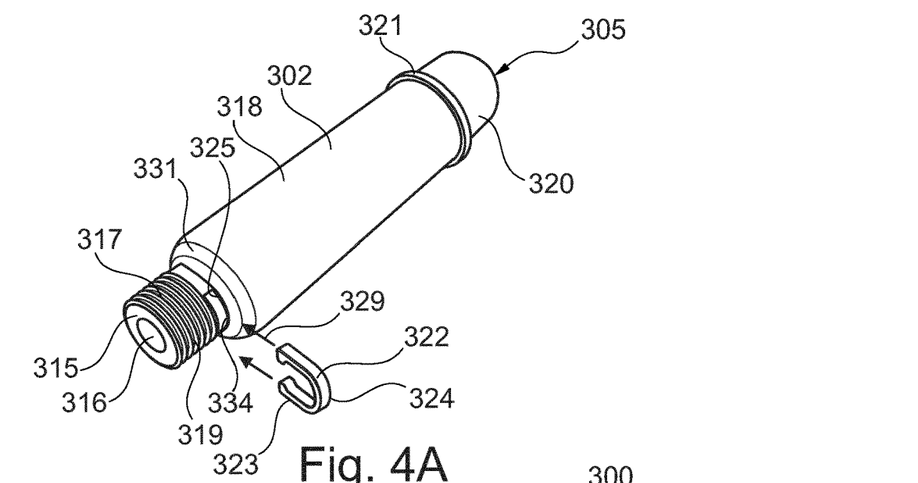
FIG. 4A shows a perspective view of the cartridge holder, right before the fixing member is mounted to the cartridge inside the cartridge holder.
Figure 4B:
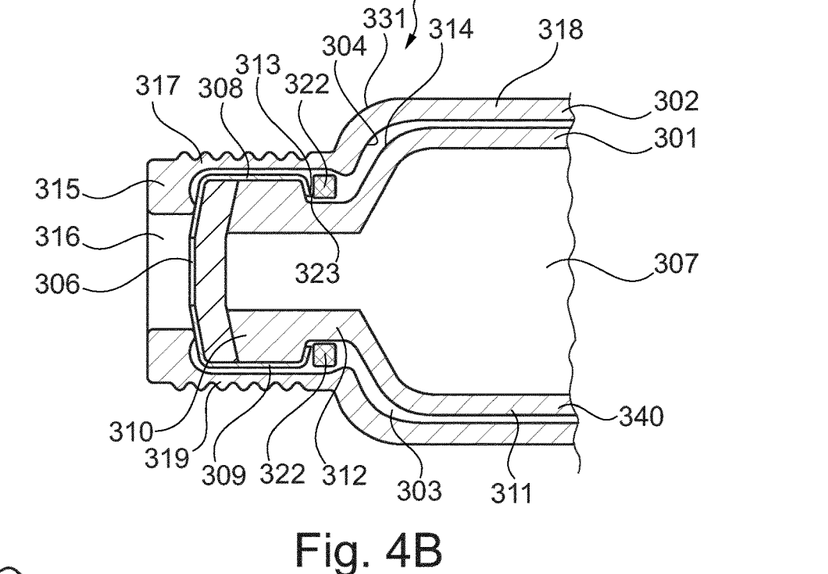
FIG. 4B shows a sectional view of a distal portion of the cartridge assembly.
Figure 4C:
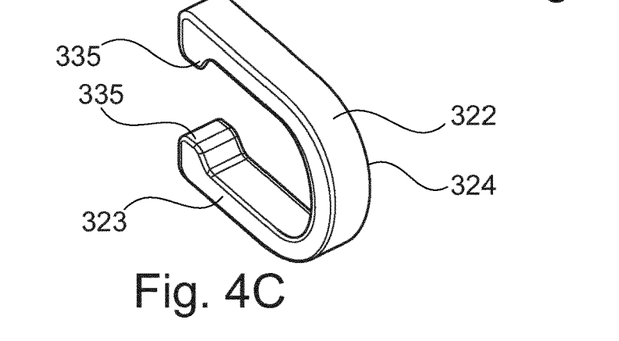
FIG. 4C illustrates the fixing member in a perspective view.

FIGS. 4A through 4C illustrate a further embodiment of a cartridge assembly 300. In the previously described embodiments, the fixing member was pre-assembled to the cartridge before the sub-assembly was introduced into the cartridge holder. In this embodiment, however, the cartridge is guided into the holder before the fixing member 322 is assembled to the cartridge.

The cartridge holder 302 comprises an opening 334 which extends radially through the entire cartridge holder wall from the exterior of the cartridge holder to its interior. The holder surface 325 may delimit the opening in the proximal direction. The fixing member 322 has a generally U-like configuration. In the region of the free ends of the legs of the U, a (radial) protrusion 335 may be provided, respectively. The protrusion(s) may reduce the width of the radial opening of the fixing member to a value which is below the outer diameter of the neck portion 312 of the cartridge. The opening 334 is preferably arranged in the distal region 317 of the cartridge holder. The opening may interrupt the needle connection feature and/or be provided in the region of the needle connector 319. Alternatively to interrupting a needle connection feature, the opening may be proximally offset from the needle connector 319. Once the cartridge 301 has been inserted into the cartridge holder 302 through the proximal opening 305 and the distal end face of the cartridge abuts a proximal face of the distal end wall 317, the fixing member 322 can be guided through the opening radially into the interior of the cartridge holder as illustrated by arrows 329. While doing so, the legs of the U may flex radially outwardly, on account of the reduced width in the region of the free end of the legs. Once they have passed the neck portion, they may flex radially inwardly again which prevents the fixing member 322 from being removed radially. The section of the fixing member with the fixing surface 324 remains in the opening 324 and, in particular, is arranged to abut the holder surface 325. If applicable, the holder surface 325 may protrude radially into the interior of the cartridge holder but preferably in a plane fashion. The opening 334 may be arranged in a region where the neck portion of the cartridge will be arranged. The axial extension of the opening may be matched to the thickness of the fixing member and/or the angular extension may be matched to the width of the fixing member 324. Protrusions 335 could also be applied in the other embodiments disclosed herein.

The fixing member 322 may be formed as a molded part, e.g. a plastic molded part, or as a metal pressing. The fixing member attaches to the cartridge from the radial direction and is unlikely to damage the septum retainer or the cartridge body which may be made of glass. As there are no flexible snap features in the axial load path (contrary to the embodiments in FIGS. 1 and 3), the fixing member 322 provides a very positive retention against axial removal of the cartridge from the cartridge holder.

As the fixing surface 323 interacts with the cartridge surface in the head portion 310 in the embodiments discussed above, cartridges with differently shaped main body portions may be secured in the cartridge holder easily, e.g. cartridges of different lengths, diameters, and/or different volumes, such as 1.5 mL and 3 mL. The head portions of the cartridges may be formed alike.

Cartridges of different volumes may have different lengths and/or different inner and/or outer diameters. The cartridge assembly may be a disposable item, which is, e.g. sold in the pharmacy. Different cartridges of the same or of different volumes may contain different drugs or drug formulations. Cartridges of a smaller volume may have a higher concentration of a drug. If the drug is insulin or an insulin derivative, for example, the cartridge of a smaller volume may have a concentration which is more than 2 times, e.g. 3 times, the concentration of drug in the larger volume cartridge. The drug or medicament in the larger volume cartridge may be formed by the same active pharmaceutical ingredient. Differences in the content between the cartridges may be, preferably only, in the concentrations of the drug or medicament within the liquid, i.e. in the specific formulation of the drug. For example, a 3 mL cartridge may comprise 300 IU (IU: International Unit), e.g. of insulin, whereas the 1.5 mL cartridge may comprise 450 IU, which, taking into account the lower volume, corresponds to three times the concentration of drug in the 3 mL cartridge.

Figure 5:
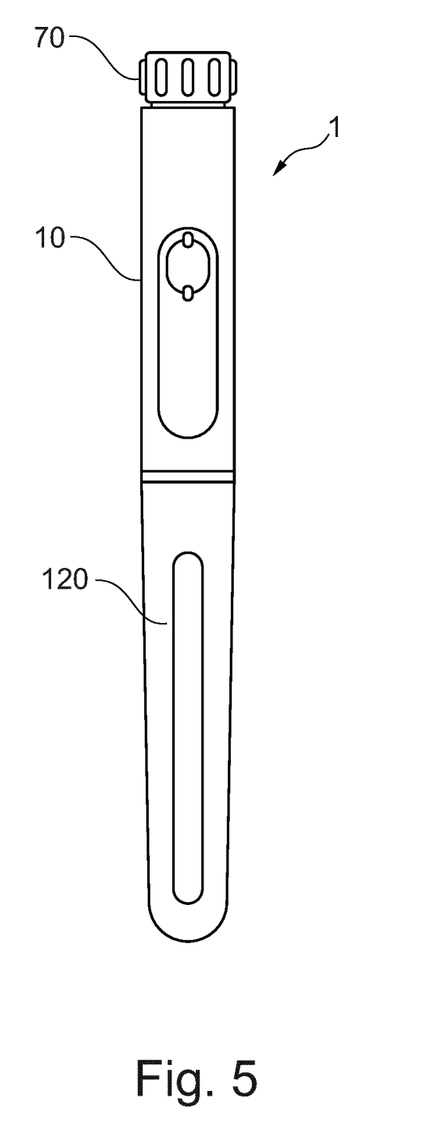
FIG. 5 illustrates an embodiment of a drug delivery device with a cap covering the distal end of the device prior to a dose setting operation.
Figure 6:
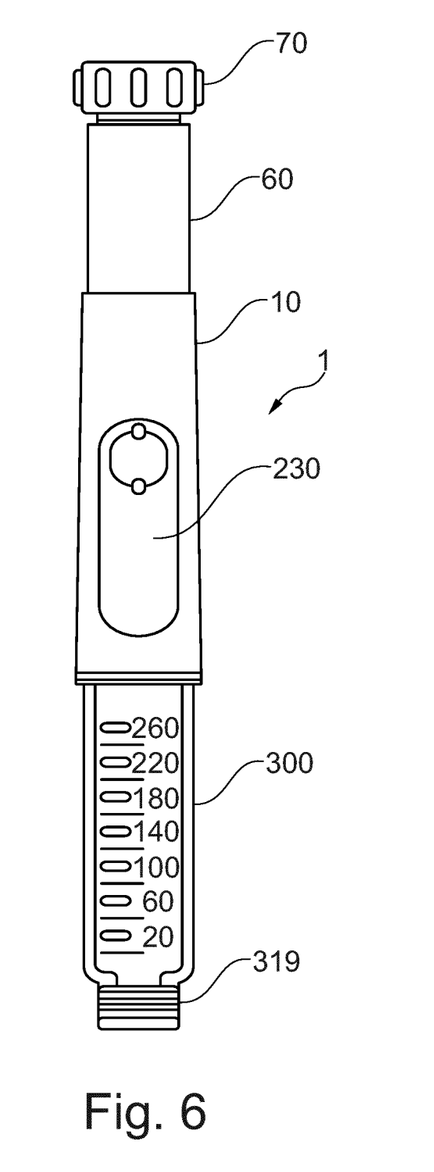
FIG. 6 illustrates the device of FIG. 5 where the cap has been removed to uncover the distal end of the cartridge assembly.

FIGS. 5 and 6 schematically illustrate embodiments of a drug delivery device suitable to be used in conjunction with the disclosed cartridge assembly. FIG. 5 shows the device 1 in a condition where a cap 120 is attached and covers the cartridge assembly 300. In FIG. 6 the cap has been removed. The cartridge assembly 300 is, expediently releasably, connected to a main body or housing 10 of the drug delivery device 1 as depicted in FIG. 6. The housing expediently defines the outer contour of the device and may be formed sleeve-like. A needle unit can be connected to the needle connector 319 in order to dispense drug or medicament from the device 1. A dose setting member 70 is movably retained in the housing 10 and can be manipulated by the user to set a dose. For example, it can be rotated relative to the housing to set a dose. The device may be a variable dose device, where the size of the dose is not predetermine by the design of the drive mechanism retained in the housing but rather may be changed by the user. In FIG. 6, a dose set condition of the drug delivery device is illustrated, where the numeral depicted in window 230 is changed as compared to FIG. 5 such that it illustrates the size of the currently set dose. The device may be designed such that during dose setting, the dose setting member 70 is displaced proximally relative to the housing 10. Alternatively, the dose setting member may stay in the same axial position independently of the set dose. From the position depicted in FIG. 6, a dispensing action may be initiated, expediently by moving or exerting a force in the distal direction onto the dose setting member 70 or a dose dispensing member provided in a proximal end section of the drug delivery device 1. To dispense the dose, the bung is displaced distally relative to the cartridge, e.g. by a piston rod of the device (not explicitly shown).

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 300 cartridge assembly
301 cartridge
302 cartridge holder
303 cartridge retaining section
304 inner wall
305 opening
306 dispensing end
307 drug/medicament
308 septum
309 septum retainer
310 head portion
311 main body portion
312 neck portion
313 cartridge surface
314 shoulder surface
315 distal end wall
316 opening
317 distal region
318 main body region
319 needle connector
320 connection region
321 step
322 fixing member
323 fixing surface
324 securing surface
325 holder surface
326 main body
327 axial opening
328 radial opening 329 arrow
330 securing feature
331 shoulder region
332 slit
333 protrusion
334 opening
335 protrusion
338 bearing surface
339 fixing feature
340 cartridge body
1 drug delivery device
120 cap
70 dose setting member
10 housing
230 window

The invention claimed is:

1. A cartridge assembly for a drug delivery device, comprising:
a cartridge containing a drug, the cartridge comprising a dispensing end;
a cartridge holder, the cartridge holder defining an interior cartridge holding section; where the cartridge is arranged within the interior cartridge holding section; and
a fixing member,
wherein the fixing member comprises a fixing surface, which is arranged to abut a cartridge surface of the cartridge, wherein the cartridge surface is a proximal surface which faces away from the dispensing end of the cartridge, and wherein the cartridge surface is arranged between the dispensing end of the cartridge and an end opposite of the dispensing end, and
wherein the fixing member comprises a securing surface which is arranged to abut a holder surface of the cartridge holder to prevent removal of the cartridge from the cartridge holder such that the cartridge is permanently secured in the cartridge holder,
wherein the holder surface is a distal surface of the cartridge holder
wherein the fixing member has a plurality of circumferentially disposed securing features, wherein each securing feature of the plurality of circumferentially disposed securing features comprises one section of the securing surface of the fixing member, wherein the circumferentially disposed securing features extend axially and radially away from a main body of the fixing member.

2. The cartridge assembly of claim 1, wherein a slit is formed between two of the plurality of circumferentially disposed securing features that are adjacent to one another such that the two of the plurality of circumferentially disposed securing features can be radially deflected.

3. The cartridge assembly of claim 1, wherein the fixing member comprises an axially extending bearing surface which bears against a neck portion of the cartridge.

4. The cartridge assembly of claim 3, wherein the axially extending bearing surface is arranged radially between an outer surface of the cartridge and the plurality of circumferentially disposed securing features.

5. The cartridge assembly of claim 1, wherein the fixing surface is a radially oriented fixing surface, and wherein the cartridge surface is a radially oriented cartridge surface.

6. The cartridge assembly of claim 1,
wherein the cartridge has a head portion, a main body portion, and a neck portion, wherein the neck portion is arranged between the head portion and the main body portion, and
wherein the fixing member has the main body, and an axial opening extending axially through the main body of the fixing member and wherein a radial width of the head portion of the cartridge is greater than a radial width of the axial opening.

7. The cartridge assembly of claim 6,
wherein the fixing member has a radial opening which extends radially from the axial opening and interrupts the main body of the fixing member, and wherein a width of the radial opening is less than a radial width of the neck portion of the cartridge.

8. The cartridge assembly of claim 6,
wherein the main body of the fixing member is closed in an angular direction.

9. The cartridge assembly of claim 1,
wherein the cartridge assembly as a whole forms one unit of consumable material.

10. The cartridge assembly of claim 1,
wherein the holder surface of the cartridge holder protrudes in an inward direction from an inner wall of the cartridge holder.

11. The carriage assembly of claim 6, wherein the neck portion has a reduced diameter as compared to the head portion.

12. The carriage assembly of claim 11, wherein the cartridge surface delimits the head portion proximally and wherein the cartridge holder has a first region in which the head portion of the cartridge is arranged and a second region that is axially offset from the first region in a proximal direction.

13. The carriage assembly of claim 12, wherein the fixing surface of the fixing member is arranged in the first region, wherein the main body portion of the cartridge is arranged in the second region, and wherein the securing surface of the fixing member is arranged in the second region.

14. A method for assembling the cartridge assembly of claim 1 for the drug delivery device, the method comprising:
providing the cartridge;
providing the fixing member;
providing the cartridge holder; and
securing the cartridge within the cartridge holder via the fixing member, wherein
the fixing member is assembled to the cartridge to form a sub-assembly and, thereafter the sub-assembly is inserted into the cartridge holder, wherein the fixing member is radially resiliently biased and deformed by mechanical cooperation with the cartridge holder before the sub-assembly reaches an end position in the cartridge holder, wherein the bias is reduced again after the deformation has taken place and before or when the subassembly reaches the end position within the cartridge holder to form the cartridge assembly.

15. The method of claim 14, wherein the bias is reduced again by an elastic restoring force that tends to re-establish a non-deformed shape, of the fixing member after the deformation has taken place and before or when the sub-assembly, reaches the end position within the cartridge holder.

16. A method comprising:
dispensing a drug from a cartridge of a cartridge assembly for a drug delivery device,
wherein the cartridge assembly comprises:
the cartridge containing the drug, the cartridge comprising a dispensing end;

a cartridge holder, the cartridge holder defining an interior cartridge holding section; where the cartridge is arranged within the interior cartridge holding section; and a fixing member, wherein the fixing member comprises a fixing surface, which is arranged to abut a cartridge surface of the cartridge, wherein the cartridge surface is a proximal surface which faces away from the dispensing end of the cartridge, and wherein the cartridge surface is arranged between the dispensing end of the cartridge and an end opposite of the dispensing end, wherein the fixing member comprises a securing surface which is arranged to abut a holder surface of the cartridge holder to prevent removal of the cartridge from the cartridge holder such that the cartridge is permanently secured in the cartridge holder, wherein the holder surface is a distal surface of the cartridge holder, and wherein the fixing member has a plurality of circumferentially disposed securing features, wherein each securing feature of the plurality of circumferentially disposed securing features defines one section of the securing surface, wherein the circumferentially disposed securing features extend axially and radially away from a main body of the fixing member.

17. The method of claim 16, wherein a slit is formed between two of the plurality of circumferentially disposed securing features of the fixing member that are adjacent to one another such that the two of the plurality of circumferentially disposed securing features can be radially deflected.

18. The method of claim 16, wherein the cartridge has a head portion, a main body portion, and a neck portion, wherein the neck portion is arranged between the head portion and the main body portion, and wherein the fixing member has the main body, and an axial opening extending axially through the main body of the fixing member and wherein a radial width of the head portion of the cartridge is greater than a radial width of the axial opening.

19. The method of claim 18, wherein the neck portion has a reduced diameter as compared to the head portion, and wherein the cartridge surface delimits the head portion proximally and wherein the cartridge holder has a first region in which the head portion of the cartridge is arranged and a second region that is axially offset from the first region in a proximal direction.

20. The method of claim 16, wherein the fixing member comprises an axially extending bearing surface which bears against a neck portion of the cartridge.

* * * * *